ically as well as in infusions as specific medi- United States Patent [19] Keplinger et al.

[11] Patent Number: 4,940,725
[45] Date of Patent: Jul. 10, 1990

[54] OXINDOLE ALKALOIDS HAVING PROPERTIES STIMULATING THE IMMUNOLOGIC SYSTEM AND PREPARATION CONTAINING THE SAME

[75] Inventors: Klaus Keplinger, Müllerstrasse 30, A-6020 Innsbruck, Austria; Hildebert Wagner, Breitbrunn am Chiemsee; Barbara Kreutzkamp, Munich, both of Fed. Rep. of Germany

[73] Assignee: Klaus Keplinger, Innsbruck, Austria

[21] Appl. No.: 333,846

[22] Filed: Apr. 3, 1989

Related U.S. Application Data

[63] Continuation of Ser. No. 195,458, May 16, 1988, Pat. No. 4,844,901, which is a continuation of Ser. No. 684,154, Dec. 20, 1984, abandoned, which is a continuation-in-part of Ser. No. 463,512, Feb. 3, 1983, abandoned, which is a continuation-in-part of Ser. No. 195,051, Oct. 14, 1980, abandoned.

[30] Foreign Application Priority Data

Oct. 7, 1980 [AT] Austria .................................. 4971/80

[51] Int. Cl.⁵ ...................... A61K 31/40; A61K 31/35

[52] U.S. Cl. ..................................... 514/411; 514/455; 514/456; 514/885

[58] Field of Search ................ 514/411, 455, 409, 885

[56] References Cited

PUBLICATIONS

Chan et al., J. Chem. Soc., C1966(24), 2245-9.
Chem. Abst., Ponglux et al., 87:44172h, 1977.
Chem. Abst., Lleander et al., 83:175457v, 1975.

*Primary Examiner*—John W. Rollins
*Attorney, Agent, or Firm*—Lorusso & Loud

[57] ABSTRACT

Tetra- and pentacyclic oxindole alkaloids, in particular the alloisopteropodine, isomer A, a pentacyclic oxindole alkaloid, are suitable for the unspecific stimulation of the immunologic system, which has been proved by a substantial percental phagocytosis increase in the granulocytic test according to BRANDT (in vitro), a substantial percental increase of the CL-response in the chemiluminescence test (in vitro) and a high increase of the phagocytosis activity of tissue macrophages of the reticoloendothelial system in the carbon-clearence-test (CCT) according to BIOZZI.

24 Claims, No Drawings

OXINDOLE ALKALOIDS HAVING PROPERTIES STIMULATING THE IMMUNOLOGIC SYSTEM AND PREPARATION CONTAINING THE SAME

BACKGROUND OF THE INVENTION

This is a continuation of co-pending application Ser. No. 195,458 filed on May 16, 1988, U.S. Pat. No. 4,844,901 which is a file wrapper continuation of U.S. Ser. No. 684,154 filed Dec. 20, 1984, now abandoned, which is a continuation-in-part of U.S. Ser. No. 463,512 filed Feb. 3, 1983 entitled "Agent for Medical Use and Preparation Thereof" which in turn is a continuation-in-part of U.S. Ser. No. 195,051 filed Oct. 14, 1980 entitled "A Method for Preparation of Agents Adapted to Change Morbid Parameters of Cell Specific Substances." European Patent No. 61.487 corresponds to these applications.

The invention relates to ozindole alkaloids of the general formula in which

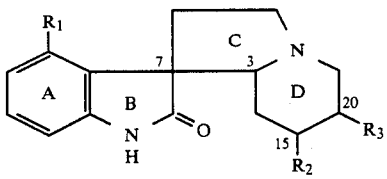

$R_1$ is an H-atom or an OH-group,
$R_2$ an oxygenated $C_3$-side-chain,
$R_3$ an ethyl- or vinyl group,
or $R_2$ and $R_3$ form together a pyran ring.

The invention further relates to a preparation containing such oxindole alkaloids from an extract, which is substantially free of tanning substances, from root parts of the Uncaria tomentosa (WILLD.) DC whose fresh bast has a yellow-brown or dark red colour.

In spite of great progresses in the theory of infectious- and tumorous diseases by antibiotics and cytostatic agents, the number of therapy-resistance infectious diseases and opportunistic infections has increased.

A small number of useful virustatic agents is available, and the therapy with cytostatic agents is handicapped by the immunosuppression which is inevitably connected herewith.

This situation has resulted in an intensive search for alternative and adjuvant methods of treatment. A concept of treatment, formerly known under the term of irritation- and stimulation therapy, today as immunostimulation, has therefore become interesting again. Most interesting in this connection is the primarily unspecific increase in humoral and cellular defense mechanisms by so called immunostimulants, i.e. by substances or substance mixtures which induce specific and unspecific endogenic defense mechanisms or intensity the immunologic response to a simultaneously administered antigen.

In various examinations certain compounds have proved to be potential immunostimulants.

Some compounds, such as polysaccharides of algae and fungi, have already been used pharmaceutically in the adjuvant therapy of tumorous diseases. It is a disadvantages of this class of compounds that most of its members are mixtures and chemically undefined. The reproducability of immunologic examinations is not guaranteed in most cases. These requirements are more likely to be fulfilled by low-molecular compounds. Most of these substances are nitrogen-containing compounds, with aristolochic acid (AS) being considered as prototype with proved immunostimulating effect. Aristolochia clematitis (Aristolochiaceae) has already been used in ancient Egypt and Greece in all kinds of wound infection. Test models have been developed (J. R. Mose and G. Lukas, *Pharmacologic Research* 11, 33, 1961), by means of which a stimulation of the endogenic defense possibilities of the organism can be proved. An extract from aristolochia clematitits prepared according to the directions of the homeopatic pharmacopoeia was used as a test extract. In the examination of the phagocytosis activity of rabbit leucocytes an increase of the phagocytosis activity to twice the initial value was observed after different dilutions of the aristolochia-extract had been injected i.v. to the animals over several days. The dilution D3 was the most effective one. After the dilution D7 no effect could be observed.

Further known compounds with stimulating effect on the immunologic system will be listed below, with the increased occurrence of potential active substances in the substance class of the N-containing compounds, the phenols, chinones and the terpenes, being striking. Almost all compounds have effects on the cellular defense.

1. ALKALOIDS
   (a) Cepharanthine (bisbenzylisochinoline alkaloid)
   (b) Berbamine (bisbenzylisochinoline alkaloid)
   (c) Matrine (lupine alkaloid)
   (d) Pilocarpine (imidazole alkaloid)
2. PHENOLS/QUINONES
   (a) 2,3-Dihydroxybenzoic acid
   (b) Ferulic acid
   (c) Forphenicine (amino acid derivative)
   (d) Anethole
   (e) Cleistanthine (lignane)
   (f) Curculigoside (phenolglucoside)
   (g) Urushiole (pyrocatechin derivates with $C_{15}/C_{17}$-side-chains)
   (h) α-Tocopherole (vitamin E)
   (i) Ubichone (mainly Q7, Q8)
   (j) Maesanine (chinone with $C_{15}$-side-chain)
3. TERPENES
   (a) Zexbrevine A/B (sesquiter-penelactone of the cermacrane type)
   (b) 12-O-Tetradeoanoyl-phorbol-13-acetate, TPA (tetracyclic diterpene)
   (c) Saponine with aglycone oleonic acid (pentacyclic (triterpene)
   (d) Cynonchoside (steroidglycoside)

It has now been found that oxindole alkaloids of the general

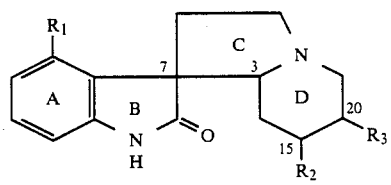

formula in which
$R_1$ is an H-atom or an OH-group,
$R_2$ an oxygenated $C_3$-side-chain,
$R_3$ and ethyl- or vinyl group, or R$_2$ and R$_3$ interact to form a pyran ring, form a further substance group with immunostimulating properties.

As taught by U.S. Ser. No. 463,512, the teachings of which are incorporated herein, root extracts from the Uncaria tomentosa (WILLD.) DC which are largely free of tanning substances and whose fresh bast has a yellow-brown or dark red colour can be used as antitumor agents, contraceptives or anti-inflammatory agents. Because of the preparation methods described therein, which are partly very similar to the isolating methods for plants alkaloids, and because of the alkaloids indicated by Hemingway et al. (*Chemical Abstracts*, Volume 82, No. 21, Ref. 135 680 k), which are contained in South-American Uncaria-species, it was possible that alkaloids would be the active substances on which the three possible uses of the root extracts, which are not directly related, are based. After further consideration that the different effects of root extracts could be caused by an unspecific stimulation of the immunologic system, the alkaloids contained in different plant parts of South-American Uncaria species were isolated therefrom and examined for their immunologic effect. In this connection such an effect could be proved with crude alkaloid fractions as well as with some of the individual isolated pure alkaloids. As particular properties stimulating the immunologic system could be proved for tetra- and pentacyclic oxindole alkaloids, such alkaloids from other Uncaria species as well as other alkaloids from different plants were examined with respect to the immunologic properties, whereby the obtained results could be supported, and the cytotoxicity of the substances with good immunostimulating effect was interesting.

SUMMARY OF THE INVENTION

Tetra- and pentacyclic oxindole alkaloids, in particular the alloisopteropodine, isomer A, a pentacyclic oxindole alkaloid, are suitable for the unspecific stimulation of the immunologic system, which has been proved by a substantial percental phagocytosis increase in the granulocytic test according to BRANDT (in vitro), a substantial percental increase of the CL-response in the chemiluminescence test (in vitro) and a high increse of the phagocytosis activity of tissue macrophages of the reticuloendothelial system in the carbon-clearance-test (CCT) according to BIOZZI.

These alkaloids may be isolated from extracts of the roots of the Uncaria tomentosa (WILLD.) D.C. whose fresh best has a yellow-brown or dark red color, from which the tanning substances have largely been removed. Alkaloids isolated from other Uncaria species, and other plants also have been found to produce specific or non-specific immunostimulations.

DETAILED DESCRIPTION OF THE INVENTION

For examining the different substances including both purified alkaloids, phenols/quinones, and terpenes and plant extracts containing these compounds with respect to immunostimulating and cytotoxic properties, the following in vitro and in vivo-test models were made:

1. Granulocytic test modified after BRANDT

Neutrophil granulocytes are together with macrophages the most important effector cells of the phagocytosis and, hence, play an important role in the resistance to infections. They represent about 60-70% of all leucocytes in the human blood. The phagocytosis effect of all these granulocytes can be measured in vitro according to a method developed by BRAND(Scand. J. Haematol. Suppl. 2, 1967) and modified by TYMPNER (Munich Med. Weekly 8, 251, 1978).

A granulocytic fraction is taken from the blood of healthy probands (PMNL—abbreviation of polymorphonuclearleucocytes)

This PMNL-fraction mainly consists of neutrophil granulocytes and few eosinophil and basophil granulocytes as well as of lymphocytes, monocytes and thrombocytes. After addition of a defined amount of yeast cells (Saccharomyces cerevisiae) and the substance to be tested incubation is carried out for 10 minutes at 37° C., the suspension is spread on an object carrier and incubated at room temperature for further 35 minutes. Then the spreads are coloured and micropscopically evaluated. 100 PMNL-cells are selected per object carrier, and it is determined how many yeast particles of the individual cells have been phagocytised. The phagocytosis index indicates the average number of phagocytised yeast particles.

Because the test simulates a part of the entity of immunologic actions, it may be assumed that the tested substances are also active in vivo, provided they get to their place of action in unchanged condition. As already mentioned, this has already been proved for aristolochic acid as low molocular compound. Little is known, however, of the course of this mechanism.

The test was carried out as follows:

preparation of granulocytic suspension 15 ml of heparinised venous blood of clinically healthy adults was diluted with 1.5% of dextran T 500 (Pharmacia) 2:1 and allowed to stand at room temperature for 30 minutes. The supernatent containing leucocytes was injected into a sterile plastic tube and centrifugated for 7 minutes at 500 r.p.m. The granulocytes in the deposit were washed twice with 5 ml of RPM I-buffer in each case. Then the granulocytes were suspended in about 5 ml of buffer and adjusted in the Neubauer's chamber to a concentration of $5 \times 10^6$ cells/ml.

Preparation of the yeast suspension

Yeast suspended in 0.9% of NaCl was heated to 100° C., three times filtered through gaze and adjusted to $3-5 \times 10^7$ particles/ml.

Preparation of the pool serum

The serum of 5 clinically healthy adults was mixed and frozen in portions of 5 ml. For the test dilution was carried out with 0.9% of NaCl 1:10.

The test was carried out as follows:

0.2 ml of substance dissolved in 0.9% of NaCl and 0.2 ml of 0.9% NaCl, as a control substance, were pipetted to 0.2 ml, each, of pool serum, granulocyte- and yeast suspension and first incubated for 10 minutes at 37° C. Then 0.5 ml of each preparation were applied to an object carrier and incubated in a humid chamber at room temperature for further 35 minutes. Granulocytes deposited, the supernatent was carefully washed with 0.9% of NaCl, and the object carrier was dried with a dryer.

Colouring:
(1) 5 min of May-Gründwald-solution (Merck), filtered, undiluted
(2) 2 min of aqua dest,
(3) 15 min of Giesma-solution (Merck), 5 ml in 180 ml H$_2$O
(4) 4 min of aqua dest. air dried Evaluation:

100 granulocytes were counted out per object carrier, and it was determined how many yeast particles of the individual cells had been phagocytised. The phagocytosis index (PJ) indicates the average number of yeast particles per granulocyte. The increase (S) of the phagocytosis activity in the blank value was calculated according to:

$$S = \frac{PJ_{substance} - PJ_{control}}{PJ_{control}} \times 100 \, (\%)$$

2. Chemiluminescence test (CL)

Although the granulocytic test according to BRANDT is a reliable method for the determination of phagocytosis-increasing properties of substances and extracts, it is very time- and staff-intensive. An alternative is the new method for measuring phagocytised cells by means of chemiluminescence.

Since ALLEN et al. (Biochem. Biophys. Res. Commun, 47, 129, 1972) invented for the first time the light emission of neutrophil granulocytes during the phagocytosis of latex particles and different bacteria and NELSON et al. (Infect. Immun 14, 129, 1976) and WEIDEMANN et al. (FEBS Letters 89, 136, 1978) were able to prove CL-phenomena on phagocytising blood macrophages (monocytes), this reaction is also applied in experimental and clinical immunology. The exact mechanism of the reaction course has not been fully clarified so far. Summin up, the CL occurring with activated phagocytes may be explained as follows: the contact of these cells with bacteria, viruses or other exogenous material, for example also chemical substances, first causes an increase in oxygen absorption. Subsequently, in the cells superoxide-anion-radicals $O_2$-are formed from the molecular oxygen, which then, either spontaneously or enzymatically catalysed, are transformed into other activated oxygen molecules, such as hydrogen peroxide ($H_2O_2$), singlet-oxygen ($^1O_2$), hydroxyl radicals ($\cdot OH$) and hydrocloride-anions ($OCL^-$). This process is called "respiratory burst".

Due to the release of the activated oxygen molecules to the immediate neighbourhood of the phagocytised cells as well as into the phagocytic vacuole itself, and due to the activation of lysosomal enzymes, microorganisms or tumor cells, which have entered, can be damaged or killed. Other molecules also take part, such as so called cationic proteins and lactoferrin. The cell walls of the microorganisms are attacked by oxydation or reduction and partly destroyed. CL occurs as a side effect as the cell wall material serves as chemiluminescence substrate for the activated oxygen molecules.

The low light yield of such CL-reactions of phagocytised cells is increased in the in-vitro-experiment by the addition of substances which are oxydated by activated oxygen and thus produce light of a certain wavelength, which can be physically measured. Suitable substrates are luminole (5-amino-2,3-dihydro-1,4-phthalazindione) and lucigenine (10,10'-dimethyl-9,9'-biacri-diniumdinitrate), which increase the CL-response by $10^3$ times.

Because of the use of sensitive measuring apparatuses in which the photons are counted by means of photomultipliers, the CL increased by the above-mentioned substances can be measured.

In the present study a 6-channel-CL-apparatus was used which allows six tests at the same time. Moreover, the apparatus, which had been used, allowed the time-dependent registration of the CL-response. Hence, the time-dependent effect could be added as third dimension to the dose-effect-curves.

For the in-vitro-examination of the phagocytosis-increasing effect of substances either purified cell populations of granulocytes or macrophages could be used, or the measurement was carried out directly in diluted whole blood. The activation of the phagocytes was effected by solid particles, e.g. opsonised bacteria, zymosan and latex particles, or by certain dissolved substances. Known activators are for example various ionophores and fluoride-ions.

The test was carried out as follows:

First orientating measurements have shown that it was difficult to reproduce the various indications of the literature for carrying out CL-measurements.

When examining the influence of substances on the phagocytosis-induced formation of activated oxygen, the CL-response depends, apart from the different activating potential of the used compounds, to a particular extent on the functioning of the phagocytes, the time of measuring and the temperature, the pH-value, the composition of the medium as well as of the CL-amplifying substance used.

All tests were carried out in 6-channel-Biolumat TM LB 9505 of Berthold, connected to an Apple TM -computer with a CL-evaluation program of Berthold.

Lucigenine was chosen for light amplification which emits photons at a narrow wavelength distribution of about 510 nm and thus almost lies in the optimum of the photo-multiplier sensitivity.

The pH-value of the measuring solution should be between 7.1 and 7.4, which is obtained by the addition of veronal-buffered salt solution. The test substances were dissolved in phosphate-buffered salt solution, (PBS-buffer). Both buffer systems contain 0.1% of glucose, because the "respiratory-burst"-reaction is connected with an increase of the glucose-metabolism.

Opsonised zymosan was used for phagocyte-activation. The measurement of the CL of isolated granulocytes was carried out with native blood of isolated polymorphonuclear leucocytes (PMNL), which had been adjusted with PBS-Puffer to $10^6$ cells/$\mu$l.

Since CL-measurements with whole blood resulted in a colour quench caused by the erthrocytes, 1:100 dilution was carried out with PBS-buffer. Thus the colour quench could be essentially reduced.

The test substances were first together with the isolated granulocytes or with the whole blood incubated at room temperature for 10 minutes and then in biclumate for 10 minutes at 37° C. After addition of the opsonised zymosan, measurement in the biolumat at 37° C. started. The CL-response of each sample was observed for 60 minutes, and the measuring values were graphically illustrated in cpm. A curve which was typical for each substance was obtained. The integrated surfaces are directly proportional to the intensity of the CL-response.

For determining the stimulation of the "respiratory-burst" of granulocytes, which had taken place, the same formula as for the granulocytic test was used.

Apparatuses

CL-measuring: Biolumat TM LB 9505, Berthold, Wildbad

Computer and diskett drive unit: Apple TM IIe, Apple Computer

Program: Berthold

Display: DM 5112 CX, Sanyo

Printer/Plotter: Epson RX-80

Preparation of the solutions:

(a) Sterile PBS-buffer without $Ca^{2+}/Mg^{2+}$, available as finished product from Biochrom, Berlin (b) Veronal-buffered salt solution with $Ca^{2+}$, $Mg^{2+}$, glucose and albumin:

Parent solution: 8.3 g of NaCl, 1.02 g of veronal, 102 mg of $MgCl_2$ and 22 mg of $CaCl_2$ were dissolved in 150 ml of $H_2O$. After addition of 3.5 ml 1 m HCl, $H_2O$ was admixed to give 200 ml.

Test solution: 40 ml of the parent solution were diluted with 140 ml of $H_2O$, adjusted to pH 7.0 with 1 m HCl and filled up to 200 ml with $H_2O$.

After addition of 200 mg of pure bovine serum albumin (Boehringer) and 200 mg of glucose, the solution was sterilized by filtration.

(c) Lucigenine-solution:

Parent solution: 25.5 mg of lucigenine were dissolved in 10 ml of $H_2O$.

Test solution: the parent solution was diluted in the ratio of 1:5 with $H_2O$.

(d) Opsonised zymosan:

Stock suspension: 25 mg of zymosan were suspended in 10 ml of 0.9% NaCl and heated in a water bath for 90 minutes. After cooling, the suspension was divided into 2 ml-portions and frozen. Test solution: 2 ml of stock suspension were incubated at room temperature for 30 minutes with 2 ml of serum of clinically healthy adults, centrifugated and washed with 0.9% NaCl. The now opsonised zymosan was suspended in 2 ml of 0.9% NaCl.

In each case aqua bidest. was used as "water".

Dilution of the whole blood 20 ml of native blood were mixed with 30 mg EDTA as anti-coagulant and diluted 1:100 with PBS-buffer.

Preparation of the polymorphonuclear leucocytes (PMNL) 20 ml of native blood were mixed with 30 mg EDTA. 15 ml of this blood were mixed with 7 ml of dextran in a syringe and allowed to stand at room temperature for 30 minutes. The leucocyte-containing supernatant was transferred into a sterile centrifugal tube and centrifugated at 1000 r.p.m. for 10 minutes. The deposit consisted of leucocytes and residual portions of erythrocytes, which can influence measurement by their colour quench. The residual erythrocytes were removed by hypotonic lyis. For this purpose, the deposit was suspended in 0.25% of NaCl-solution and agitated on the whirlmix for 20 seconds. Then 20 ml of 1.6% NaCl-solution were admixed and agitated again. After centrifugation at 2000 r.p.m. for 10 minutes, the supernatant was sucked off and the whole process war repeated twice. Subsequently, the deposit was suspended in 2 ml of PBS-buffer and diluted 1:10 with Türcks-solution. It was adjusted in the Neubauer's chamber with PBS-buffer to $10^6$-cells/ml.

The test was carried out as follows (a) whole blood:

460 μl of veronal-buffered salt solution

200 μl of diluted whole blood

100 μl of lucigenine-solution

200 μl of substance dissolved in PBS and PBS as control (b) PMNL:

630 μl of veronal-buffered salt solution

15 μl of PMNL

100 μl of lucigenine-solution

200 μl of substance dissolved in PBS and PBS as control

After preincubation at room temperature for 10 minutes and subsequent incubation for 10 minutes at 37° C. in 6-channel-Biolumat ™, 40 μl of opsonised zymosan were admixed under thorough stirring and measurement was started. Measuring was stopped after 60 minutes.

Evaluation of the test results.

The CL-response of the samples was stored by a computer over the measuring period, and after measurement illustrated in the form of a curve. By integration of the surfaces, the intensity of the CL-response of the respective sample was obtained in cpm.

The increases S of the CL-response by a test substance was calculated according to $$S = \frac{cpm_{substance} - cpm_{control}}{cpm_{control}} \times 100 \, (\%)$$

According to the literature it could be assumed that all extracts and substances with positive reactions in the granulocytic test according to BRANDT would give a positive result in the CL-test, too. It was unknown how far the two measuring results correlated with each other and how exact the CL-method is compared to the granulocytic test. Moreover, CL-measurement with isolated granulocytes had to be compared with the whole blood method.

For CL-examinations on the pure substances we have chosen the Na-salt of the aristiolochic acid as the phagocytosis-increasing effect is secured for this compound, and we already had concentration-effect-datas from the granulocytic test.

Accuracy, reproducability and sensitivity of the granulocytic- and whole blood-method:

As expected, the measurement at isolated granulocytes with a relative variation coefficient of 7-8% proved to be the preciser method, whereas with whole blood a variation of the mean values of about 16% were obtained.

With the PMNL-method a significant increase of the CL-response could still be registered in dilutions of $10^{-9}$%.

In contrast thereto, the whole blood-method was far less sensitive. Only at a concentration of $10^{-3}$% an increase was measurable. Lower concentrations gave very low counting yields only.

This might essentially be caused by the quench effect of the erythrocytes which is still present in spite of the dilution of the whole blood. The cpm of the control lie in this test substantially below those of the PMNL-test.

Through these results the ranges in which the two CL-methods can be applied are defined. The whole blood method, which can quickly be carried out, is only suitable for the preselection of substances with immunostimulating effect. Dose-effect-curves can only be made, however, by means of CL-measurement with isolated granulocytes.

Percental increase of the CL-response with the whole blood- and PMNL-method, test substance aristiolochic acid

|  | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ | (%) |
|---|---|---|---|---|---|---|---|---|---|---|
| whole blood | — | 51,9 | 19,2 | 21,8 | 14,0 | 5,5 | — | — | — | |
| PMNL | — | — | 85,1 | 93,5 | 68,3 | 61,9 | 58,7 | 31,3 | — | |

Comparison between CL-method and granulocytic test: as in the granulocytic test, a dose-dependent increase of the phagocytosis activity in form of the "respiratory burst" reaction has also been found in the CL-test with isolated granulocytes. The CL-response of different aristolochic acid-concentrations will be given below. The results of these measurements correlated quite good with those of the granulocytic tests. Only the efficiency maximum was in the CL-test with a concentration of $10^{-5}$% lower by a power of ten than in the granulocytic test.

Increase of the CL-response of different aristolochic acid-concentrations

| Channel | Concentration (%) | Peak-Maximum (cpm × $10^5$) | $t_{max}$ (min) | Increase of CL-response |
|---|---|---|---|---|
| 1 | control | 2.12 | 50.0 | — |
| 2 | $10^{-4}$ | 4.80 | 30.0 | 126.4 |
| 3 | $10^{-5}$ | 5.52 | 32.6 | 160.3 |
| 4 | $10^{-6}$ | 3.40 | 34.6 | 69.8 |
| 5 | $10^{-7}$ | 3.24 | 32.0 | 52.8 |
| 6 | $10^{-8}$ | 4.10 | 29.3 | 93.4 |

The percental numbers calculated according to the same formular in the granulocytic- and CL-test can however not be compared directly because the measuring principles of the two methods are different.

A comparison of the dose-effect-curve of aristolochic acid in the granulocytic- and CL-tests showed a good consistency of the curve paths of the two test methods.

According to our examinations the CL-method with isolated granulocytes can fully replace, with respect to accuracy as well as sensitivity, the labour-intensive granulocytic test according to BRANDT, with a still more detailed description of the phagocytosis processes being possible because of the registration of the time-dependent stimulation.

3. Carbon-clearance-test (CCT) according to BIOZZI

By means of this in-vivo-test developed by BIOZZI et al (C. R. Soc. Biol. 148, 431, 1954) (Progr. Liver Dis. 2, 166, 1965) the phagocytosis activity of tissue macrophages of the reticulor-endothelial system (RES) is determined. Gelatine-stabilized carbon particles are intravenously injected to test animals, blood is taken from the retro orbital venous plexus at certain intervals, and the elimination of the carbon by photometric turbidimetry is determined. The Kupffer's cells of the liver participate with 90% in the elimination of exogenous particles, the macrophages of the spleen participate with 10%.

The exponential course of the carbon elimination can be illustrated by a straight line (log E against t) whose negative slope is the regression coefficient K. If a potentially stimulated substance is once or several times given into a certain concentration a certain time before the test starts, e.g. 24 or 48 hours, a phagocytosis increase can be concluded by comparison of the regression coefficient with the blank value. If the relation is $K_{subst.}/K_{control} < 1$, the test substance has a suppressive effect on the phagocytosis activity. If the relation is $> 1$ stimulation has taken place.

The regression coefficient K of the carbon elimination differs from individual to individual dependent on the weight of the liver and spleen so that the true elimination constant ($\alpha$-value) can be found only after incorporation of these figures. Our examinations with different substances have shown that the quotients of the $\alpha$-values hardly differ from the quotients of the K-values.

Test animals: female NMRL-mice, 25-30 g

Collective number: for screening examinations 3 animals, otherwise 5 animals per substance, 2 animals for control maintenance and feeding: at 20°-22° C. in makrolon cages, SFI-standard feed, water ad libitum method of treatment: the substance dissolved in 0.9%. NaCl was i.p. administered once or several times. The solution should be membrane-filtered to avoid cell-stimulation by fine suspension. Intraperitoneal administration of coarse suspensions is lethal to the animals. The individual dose was normally between 0.1 and 10 mg/kg body weight. Last administration was carried out 24 hours before the start of the test.

The test was carried out as follows:

An ink suspension containing a 10% gas black (particle size 200-250 A) was adjusted to 16 mg of carbon per ml by means of 1% gelatin in 0.9% of NaCl and preheated to 37° C. Each mouse was injected 0.1 ml/10 g into the tail vein. After t=3, 6, 9, 12, 15 min 25 $\mu$l of blood was punctured from the retroorbital venous plexus (heparinised one way—micro-pipettes). The blood was hemolysed in 2 ml of aqua dest. and the carbon concentration was photometrically determined at $\lambda$=650 nm (Hitachi-spectrometer 181, cell thickness 1 cm).

Evaluation: For the carbon elimination which has an exponential course, the regression coefficient K was mathematically determined (log E against t). By formation of the quotient $D_{subst.}/K_{control}$ the stimulation or suppression of the RES could be concluded.

4. Lymphocytic transformation test

In the lymphocytic transformation test the induction of the blasto-transformation of normal lymphocytes and their subsequent mitosis is measured. For this purpose the substance to be examined is incubated with isolated lymphocytes or with diluted whole blood, the samples are marked with $^{14}$C- and $^3$H-thymidine and incubated again. The marked thymidine incorporated into the cell-DNA is measured on the liquid-scintillation-spectrometer.

5. Cytotoxicity test by the $^3$H-thymidine-incorporation test on ascites cells

Since in the granulocytic test some substances lyse the granulocytes at high concentrations we examined the cell-damaging effect at the model of the $^3$H-thymidine-incorporation test in ascites cells to be able to find a possible relation between the phagocytosis increase and cytotoxicity in potential active substances.

In this in-vitro-test system according to WEITZEL et al (Hoppe-Seyler's Z. physiolog. Chem. 348, 433, 1967) the cytotoxicity of substances by inhibition of the DNA-synthesis of tumour cells can be numerically determined by the changed incorporation rates of $^3$H- thymidine in ascites cells of Walter-250-carcinosarcoma of rats.

The test was carried out as follows:

3 ml of cell suspension of Walker-250-carcinosarcoma-ascites were mixed with 10 ml of MEDIUM L-15 (Boehringer) in a 50 ml centrifugal glass and centrifugated for 10 minutes. The supernatant was decanted and the centrifugal glass was filled up with medium to 1 cm below the rim. From the stirred cell suspension 1 ml (corresponds to $2 \times 10^6$ cells/ml) per sample was given into a centrifugal glass and 500 µl of the test solution were added, the control test was carried out with 500 µl of medium. Each test was carried out between four and six times. After a preincubation of two hours at 37° C. 100 µl of $^3$H-thymidine (spec. act. 50 Ci/nM) were added per sample and incubated under agitation for a further hour. Then the incorporation was stopped by addition of 1.5 ml of 1 N-perchloric acid per sample, and the preparation was stored in the fridge overnight. The deposits, which contained the incorporated precursors, were sucked off by a filter paper moistened with perchloric acid, washed with 5% trichloroacetic acid and washed again with ethanol. The filters were given in polyethylene flasks and the activities were measured in toluene-scintillator. The results were compared with the control, and the inhibition effect was given in per cents.

Comparison of the test results

Since the percental incorporating inhibition with identical substances showed variations of up to 30% between individual tests, Methotrexat ®, N-[4-[[(2,4-Diamino-6-pteridinyl) methyl]methyl amino]benzoyl]-L-glutamic acid which inhibits the DNA-snythesis as folic acid antagonist, was contested as reference substance in each test series. The mean value of the Methotrexat ®-inhibition (43% with 2 mg/ml) was used for determining the relative inhibition H of the substances.

$$H_{subst.} = \frac{H_{subst.test}}{H_{meth.test}} \times H_{meth.mean\ value}\ (\%)$$

By comparing the found values with the results of the granulocytic test considerations which had been made with other low-molecular compounds could be confirmed, according to which substances which are cytotoxically active at high concentration have a stimulating influence on the phagocytosis effect of isolated granulocytes when further diluted to $10^{-2}$ or $10^{-3}$%. How far this statement can be generalized and if it can also be applied to higher-molecular compounds must be clarified by further examinations.

6. Acute toxicity

Test animals: female or male NMRI-mice, 30-35 g maintenance and feeding: at 20°-22° C. in makrolon cages, SFI-standard feed, water at libitum collective number: 5 mice The test was carried out as follows: test substances dissolved in H$_2$O or 0.9% NaCl-solution were administered to the mice o.o. by means of a probang or i.p. The behaviour with respect to a control group was observed for 14 days.

A prerequisite in all tests was a clear solubility of the test material. In the examination of lipophil extracts and substances the compounds, such as carboxymethylcellulose or dimethylsulfoxid, which are added as solubilizers, are used as reference value in the tested concentration, because the solubilizers are partly self-stimulating.

In the CCT the use of DMSO is not recommended because of the high toxicity.

Moreover, the test solution should be prepared free of germs to the greatest possible extent. Grampositive bacteria contain in their cell walls polysaccharides which may partly have a stimulating influence on the phagocytosis effects of granulocytes. The lipopolysaccharides of cell walls of gramnegative bacteria, so called endotoxines, may also influence the test result. Living bacteria and bacteria extracts show a high RES-stimulating effect. Furthermore, some endotoxines have side effects, such as pyrogenicity, antigenicity and toxic metabolic changes, which may also be disturbing in the CCT.

It is therefore advisable to sterilize the test solution by filtration and to store it in the fridge.

For localising the effective principle of the oxindole alkaloids according to the invention, water- and ethanol extracts of untreated and NH$_3$-alkalised powder of the Uncaria tomentosa, whereby a stimulation by NH$_3$ alone had previously been excluded, further raw alkaloid mixtures obtained from Uncaria tomentosa, pure alkaloids isolated therefrom as well as other oxindole alkaloids were tested.

For the preparation of the extracts the pulverized, dried drug which was alkalized with 10% NH$_3$ was mixed with the eluant at a ratio of 1:10, extracted for two days at room temperature on a magnetic stirrer, filtered and the filtrate was concentrated to dryness.

The raw alkaloid mixture was prepared according to the following methods. The dried herb material was thoroughly moistened with 10% NH$_3$, allowed to stand for one hour at room temperature and carefully dried under IR-light. Then, the drug was macerated with ethyl acetate for four days on the magnetic stirrer. The thus obtained raw extract was concentrated and extracted with 2% H$_2$SO$_4$ until the aqueous phase showed no more positive Valser-reaction. The aqueous phase was then mixed with solid Na$_2$CO$_3$ until alkaline reaction at pH 8-9. By means of repeated extraction of the aqueous phase with ethyl acetate 750 g of the drug became 6.75 g of a light brown coloured raw alkaloid mixture, corresponding to a yield of 0.9%. Then conversion into the hydrochloride form took place.

The individual oxindole alkaloids were isolated and identified from the raw alkaloid mixture.

They were as follows:

1. allo-isopteropodine, isomer A having the formula C$_{21}$H$_{24}$O$_4$N$_2$, MG:368 m.p.: 204°-209°

Thin-layer chromatography: R$_f$ 0.73 (LM I); 0.48 (LM II); 0.83 (LM III)

HPLC: Rt 8.8 min (TS I)

$[\alpha]_D^{20}$: −85.1 (c=0.554/CHCl$_3$)

UV (MeOH)=$\lambda_{max}$=208, 243, 283 (sh)

mass spectrum: m/e (rel.int.): 368 (M$^+$, 100), 223(70), 208(35), 180(14), 146(11), 145(9), 144(5), 130(25), 69(45)

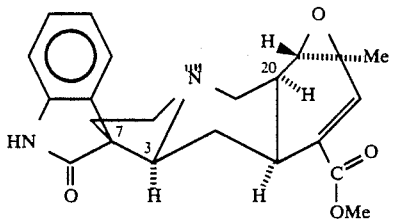

2. allo-pteropodine, isomer B having the formula C$_{21}$H$_{24}$O$_4$N$_2$, MG: 368
m.p.: 214°–219° C.
Tlc: R$_f$ 0.72 (LM I), 0.47 (LM II), 0.81 (LM III)
HPLC: Rt 0.8 min (TS I)
UV (MeOH): $\lambda_{max}$=208, 243, 283 (sh)
mass spectrum: m/e (rel.int.): 368 (M$^+$, 100), 223(84), 208(25), 180 (20) 146(8), 145(11), 144(11), 130(14), 69(35)

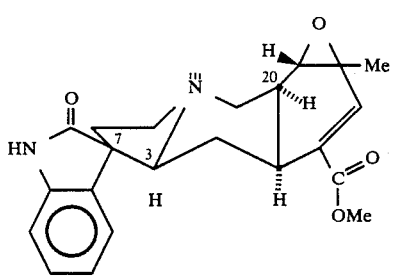

3. normal-isomitraphylline, isomer A having the formula C$_{21}$H$_{24}$O$_4$N$_2$; MG 368
m.p.: 96°–106° C. (Z)
Tlc: R$_f$ 0.71 (LM I), 0.47 (LM II), 0.80 (LM III)
HPLC: Rt 9.2 min (TS I)
$[\alpha]_D^{20}$: +145° (c=0.758/CHCl$_3$)
UV (MeOH): $\lambda_{max}$=208, 243, 283(sh)
MS: M/e (rel.int.):368 (M$^+$, 70), 223 (100), 208(10), 180(4), 146(6), 145(5), 144(7), 130(11), 69(29)

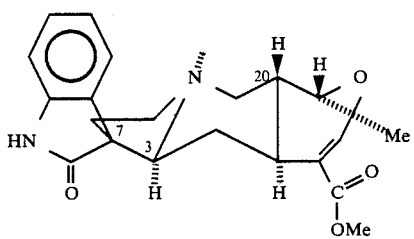

4. normal-isorhynchophylline, isomer A having the formula
C$_{22}$H$_{28}$O$_4$N$_2$, MG: 384
m.p.: 138°–141° C.
Tlc: R$_f$ 0.71(LM I), 0.42 (LM II), 0.70 (LM III)
HPLC: Rt 13.9 min (TS I)
$[\alpha]_D^{20}$: +7.8° (c=0.420/CHCl$_3$)
UV (MeOH): $\lambda_{max}$=208, 243, 283 (sh)
mass spectrum: m/e (rel.int.): 384 (M$^+$, 100), 239(80), 224(23), 210(14), 208(25), 146(6), 145(7), 144(10), 130(14), 69(75)

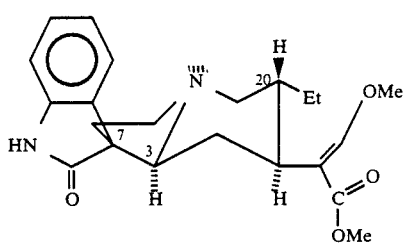

5. normal-mitraphylline, isomer B having the formula C$_{21}$H$_{24}$O$_4$N$_2$, MG: 368
m.p.: 264°–268° C.
Tlc: R$_f$ 0.55 (LM I), 0.39 (LM II), 0.50 (LM III)
HPLC: Rt 10.4 min (TS I)
$[\alpha]_D^{20}$: −4.3° C. (c=0.587/CHCl$_3$)
UV (MeOH): $\lambda_{max}$=209, 243, 283 (sh)
mass spectrum: m/e (rel.int.): 368 (M$^+$, 60), 223(100), 208(10), 180(4), 146(6), 145(7), 144(10), 130(10), 69(27)

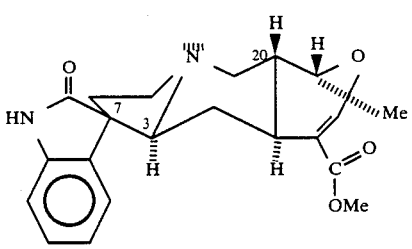

6. normal-rhynchophyllin, isomer B having the formula C$_{22}$H$_{28}$O$_4$N$_2$, MG: 384
m.p.: 214°–216° C.
Tlc: R$_f$ 0.36 (LM I), 0.25 (LM II), 0.31 (LM III)
HPLC: Rt 17.3 min (TS I)
$[\alpha]_D^{20}$: −15.1° (c=0.551/CHCl$_3$)
UV (MeOH): $\lambda_{max}$=208, 243, 283(sh)
mass spectrum: m/e (rel.int.): 384 (M$^+$, 100), 293(80), 224(30), 210(20), 208(24), 146(8), 145(12), 144(13), 130(10), 69(90)

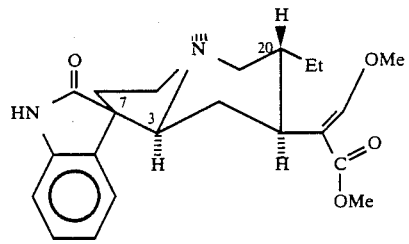

Applied solvent mixtures (LM) for Tlc
LM I chloroform-acetone (5:4)
LM II chloroform-ethanol (95:5)
LM III ethylacetate-isopropanol-NH$_3$ conc. (100:2:1)

Further to these oxindole alkaloids isolated from Uncaria tomentosa, the oxindole alkaloid speciophylline which is also contained in Uncaria-species and has the formula

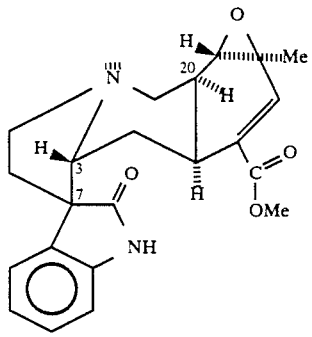

and the oxindole alkaloid gelsemine which is known as one of the main component substances of the root of Gelsemium semervirens (loganiaceae) were used for at least a part of the immunologic examinations.

For preparing the water-soluble hydrochloride form, the free alkaloid bases were dissolved in ether and HCl-gas was introduced from a gas bomb. The hydrochlorides precipitated white. The ether was separated, the hydrochloride was washed again with unhydrous ether and then dried over phosphorpentoxide in the vacuum desiccator.

The following percental phagocytosis increases of the various extracts and substances could now be proved in the granulocytic test, with different concentrations being used in each case:

| Concentration | $10^{-2}$ | $10^{-3}$ | $10^{-4}$ | $10^{-5}$ | $10^{-6}$ | $10^{-7}$ |
|---|---|---|---|---|---|---|
| 1. Extracts form *Uncaria tomentosa* | | | | | | |
| H₂O-macerate | 7.3 | 21.8 | 24.1 | 5.7 | — | — |
| H₂O-macerate (NH₃) | 15.6 | 12.9 | 29.6 | 28.4 | — | — |
| EtOH-macerate | — | 14.4 | 12.0 | 26.3 | — | — |
| EtOH-macerate (NH₃) | 7.6 | 35.6 | 36.8 | 25.5 | — | — |
| 2. Raw alkaloid mixture from *Unc. tom* | 20.1 | 21.0 | 15.7 | 10.3 | — | — |
| 3. Oxindole alkaloids isolated from *Unc.tom.* | | | | | | |
| Isopteropodine | 23.4 | 48.7 | 55.9 | 38.2 | 28.2 | 13.6 |
| Pteropodine | 11.2 | 21.7 | 26.1 | 23.0 | — | — |
| Isomitraphylline | 16.5 | 27.0 | 27.0 | 19.4 | 5.7 | — |
| Isorhynchophylline | 10.8 | 25.2 | 27.3 | 16.1 | 8.8 | — |
| Mitraphylline | — | — | — | — | — | — |
| Rhynchophylline | — | — | — | — | — | — |
| 4. Other oxindole alkaloids | | | | | | |
| Speciophylline | 10.5 | 18.5 | 26.0 | 35.3 | — | — |
| Gelsemine | 22.1 | 40.4 | 33.7 | 8.2 | — | — |

Cytotoxicity was found in most cases in the concentration $10^{-1}\%$.

For comparison, the granlocytic test was also carried out with non-oxindole alkaloids.

The isochinoline alkaloid berberine, which is above all used for virus inflammations of the eye, was inactive up to a concentration of $10^{-4}\%$.

With vincristine (indole alkaloid of the aspidospermine type) and with camotothecine (chinoline alkaloid) no effects have been found, either, up to dilutions of $10^{-6}\%$. These compounds are mitose-inhibitors and used as cancerostatic agents. For vincristine, even an in-vitro-inhibition of the macrophage-phagocytosis has been found at concentrations of $10^{-4}\%$ and $10^{-5}\%$.

The chinolizindine alkaloid cytisine and sparteine, main alkaloids of the whole plant of Baptisia tinctoria (Fabaceae) used against septic diseases and ulcers did not show any effect, either, up to concentrations of $10^{-4}\%$.

The tests with the bisbenzylisochinoline alkaloid thalifaberine, thalifabine and huangshanine (tested up to $10^{-4}\%$) isolated from Thalictrum faberi (Ranunculaceae) were also negative, although the plant has been used in Chinese folk-medicine as antiphlogistic agent and for the treatment of stomach cancer.

Among the pure alkaloids isolated from the alkaloid mixture clear differences in effect were found, although the maximum effects lay uniformly in the concentration range of $10^{-2}\%$ - $10^{-5}\%$. The results found in the granulocytic test according to BRANDT have substantially been confirmed by the chemiluminescence-test. The reason for some variations between the two test results (e.g. with isorhynchophylline) have not been found yet. The following table shows the percental increase of the CL-response of the raw alkaloid mixture and of the oxindole alkaloids isolated from Uncaria tomentosa

| Concentration | $10^{-2}\%$ | $10^{-3}\%$ | $10^{-4}\%$ | $10^{-5}\%$ | $10^{-6}\%$ | $10^{-7}\%$ | $10^{-8}\%$ |
|---|---|---|---|---|---|---|---|
| 1. Alkaloid mixture | — | 31.5 | 35.5 | 75.2 | 33.2 | — | — |
| 2. Isolated alkaloids | | | | | | | |
| Isopteropodine | — | 67.2 | 66.0 | 55.7 | 68.1 | 55.3 | 31.2 |
| Pteropodine | — | 10.6 | 10.0 | 23.7 | 15.4 | — | — |
| Isomitraphylline | — | 15.4 | 15.7 | 36.1 | 46.7 | 18.6 | — |
| Isorhynchophylline | — | — | — | — | — | — | — |
| Mitraphylline | — | — | — | — | — | — | — |
| Rhynchophylline | — | — | — | — | — | — | — |

Stalk extracts of the examined Uncaria-species, which all contain low alkaloid amounts, did not show a high phagocytosis activation in the case of average increase rates between 10% and 20%.

In contrast thereto, the isopteropodine-containing roots showed values between 30% and 40% activity increase on the average.

The leaves with similarily high alkaloid concentrations like the roots showed a differentiated picture. While examples of the 1983 harvest, which contained no ispteropodine, obtained only slightly higher stimulating values than the stalk, leaves harvested in 1981 showed again increase rates of between 30% and 40%. These leaves contained isopteropodine at about the same concentration as the roots.

Apart from the alkaloid content of the drug, the effectiveness therefore also depends on the alkaloid pattern, with the different phagocytosis increase rates of the individual alkaloids being identifiable in the total result.

The examination of the raw alkaloid mixture in the water-soluble hydrochloride form showed an average phagocytosis increase of 20%. As the latter-mentioned was not as high as the one of the ethanolic total extract, the accompanying substances present in the aqueous and ethanolic extract seem to have an adjuvant role in the sense of an increase in effect. This fact was confirmed when 10 ml of an 1% aqueous solution of a water-soluble catechine extract (pH 6.0) was mixed with 10 ml of a 0.1% aqueous solution of the total alkaloid mixture, stirred for 24 hours at room temperature on the magnetic stirrer, freeze-dried and finally examined in the carbon-clearance test.

The results of all samples tested by us in the carbon-clearance-test according to BIOZZI have been summarized in the following table.

Like in the granulocytic test, it can be found in this test, too, that the alkaloids participate in the effectiveness. An alkaloid-containing aqueous macerate stimulated the RES to a higher extent than an aqueous macerate having a low alkaloid content. When the alkaloid mixture was applied together with catechine, which does not stimulate itself, an activity increase was obtained which was similarily high as in the case of the aqueous macerate.

The test for cytotoxicity was carried out with the $^3$H-thymidine-incorporation test on ascites cells. Different extracts and alkaloid concentrations were examined.

Percentral incorporating inhibition of extracts and alkaloid concentrations from Uncaria tomentosa in the $^3$H-thymidine incorporation test (a) Comparison of the cytotoxicity with a dosage of 0.2%

| Sample | relative incorporating inhibition (%) |
|---|---|
| H$_2$O-extract | 42 |
| H$_2$O-extract of the alk. drug | 65 |
| MeOH-extract | 52 |
| MeOH-extract of the alk. drug | 64 |
| Total alkaloid mixture | 70 |
| P1-HCl | 100 |
| P2-HCl | 69 |

(b) Percental incorporating inhibition at different concentrations

| Alkaloid-HCl | $10^{-1}$% | $10^{-2}$% | $10^{-3}$% | $10^{-4}$% | $10^{-5}$% |
|---|---|---|---|---|---|
| Total alkaloid mixture | 67 | 36 | 38 | 12 | — |
| P1 | 93 | 86 | 45 | 15 | 15 |
| P2 | 64 | 58 | 20 | — | — |

| Sample | Dose | Application | Regression-coefficient K | $\frac{K_{subst.}}{K_{control}}$ |
|---|---|---|---|---|
| alkaloid-containing aqueous macerate from Unc.tom. | 10 mg/kg | i.p. 1 × 24 hrs. before test start | −0.050 | 2.3 |
| low-alkaloid aqueous macerate form Unc.tom. | 10 mg/kg | i.p. 1 × 24 hrs. before test start | −0.046 | 1.7 |
| alkaloid mixture-HCl | (a) 0.1 mg/kg (b) 0.001 mg/kg | i.p., 5 ×, last dose 24 hrs. before test start | (a) −0.017 (b) −0.037 | (a) 0.3 (b) 0.7 |
| alkaloid mixture together with an aqueous catechine extract | 10 mg + 1 mg/kg | i.p. 1 × 24 hrs. before test start | −0.060 | 2.2 |
| aqueous catechine extract | 10 mg/kg | i.p. 1 × 24 hrs. before test start | −0.021 | 1.0 |

Lymphocytic transformation test

An aqueous total extract from Uncaria tomentosa was examined, the raw alkaloid mixture from Uncaria tomentosa, and two mixtures P1 and P2 were examined. P1 contains the alkaloids isopteropodine, pteropodine, isomitraphylline and isorhynchophylline, which are active in the granulocytic test, P2 contains the alkaloids mitraphylline and rhynchophylline which are not active.

Neither in the whole blood method nor in the measuring with isolated lymphocytes any of the examined substances showed an increase of the $^3$H-thymidine-incorporation exceeding beyond the spontaneous transformation.

Acute toxicity, cytotoxicity and antitumor effect

The test for acute toxicity was made on mice with an aqueous total extract from Uncaria tomentosa and a raw alkaloid mixture. The extract was perorally applied at a maximum concentration of 5 g/kg body weight and intraperitoneally at a maximum concentration of 2 g/kg. The alkaloid mixture was administered orally up to 2 g/kg and intraperitonally up to 1 g/kg. The mice were observed over a period of 14 days and no changes from their normal behaviour were found.

As can be seen, the alkaloid enrichments at concentrations of $10^{-1}$% have cytotoxic effects. The toxicity decreases when dilution increases.

These results correlate with the cytototoxicity examinations of the alkaloid enrichments P1 and P2, in which KB- and P 388-cells served as test models. At concentrations of up to 5 µg/ml the growth of both cell types was not influenced. Only at a dosage of 50 µg/ml ($5 \times 10^{-3}$%) both samples had a slightly cytotoxic effect:

| Cytotoxicity of P1 and P2 on KB- and P 388-cells | | | | | |
|---|---|---|---|---|---|
| | 0.5 | | 5.0 | | 50 (µg/ml) |
| Alkaloid mixture | KB | P 388 | KB | P 388 | KB | P 388 |
| P1-HCl | 100 | 100 | 100 | 100 | 77 | 76 |
| P2-HCl | 100 | 100 | 100 | 100 | 77 | 64 | the percental survival rate of the cells is indicated

Both cytotoxicity tests confirm the correlation between cytotoxicity and immunologic stimulation. The total alkaloid mixture for example at a concentration of $10^{-1}\%$ lyses the granulocytes. In further dilutions, which have no or almost no more cytotoxic effect, immunologic stimulation can be observed. It is interesting that in the $^3$H-thymidine-incorporation test the mixture P2 together with the alkaloid mitraphylline and rhynchophylline, which are inactive in the granulocytic test, is less toxic than the mixture P2 with the active alkaloids.

I claim:

1. A pharmaceutical agent for stimulating the immunological system comprising oxindole alkaloids with the formula $C_{21}H_{24}O_4N_2$, derived from Uncaria tomentosa (WILLD.) DC. of the order of Gentianales having a yellow-brown or dark red fresh bast and substantially free from tannin substances, said oxindole alkaloids being selected from the group consisting of isopteropodine and pteropodine, wherein at least one of said oxindole alkaloids is further complexed with a catechine to form an alkaloid-catechine complex.

2. A pharmaceutical agent according to claim 1 wherein at least one oxindole alkaloid is an isomer of the allo-series.

3. A pharmaceutical agent according to claim 1 wherein each oxindole alkaloid is in the hydrochloride form and present as an aqueous solution having a concentration of between $10^{-3}\%$ and $10^{-6}\%$.

4. A pharmaceutical agent according to claim 1 wherein at least one oxindole alkaloid is selected from the group consisting of:

allo-isopteropodine, isomer A having the formula

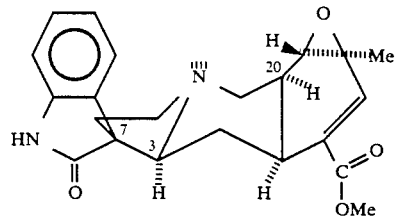

and allo-pteropodine, isomer B having the formula

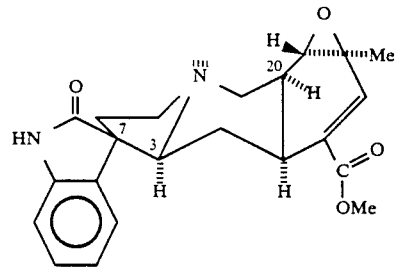

5. A pharmaceutical agent according to claim 1 wherein said alkaloid-catechine complex is produced from a ratio of ten parts by volume of aqueous catechine extract to one part by volume of aqueous oxindole alkaloid solution.

6. A pharmaceutical agent for stimulating the immunological system comprising oxindole alkaloids with the formula $C_{21}H_{24}O_4N_2$, said oxindole alkaloids being selected from the group consisting of isopteropodine and pteropodine, wherein at least one of said oxindole alkaloids is further complexed with a catechine to form an alkaloid-catechine complex, said pharmaceutical agent comprising an extract of root parts of the Uncaria tomentosa (WILLD.) DC. of the order of the Gentianales having a yellow-brown or dark red fresh bast, said extract being substantially free from tannin substances and dissolved in a pharmaceutical carrier selected from the group consisting of water and alcohol to form the pharmaceutical agent.

7. The pharmaceutical agent according to claim 6 wherein at least one oxindole alkaloid is an isomer of the allo-series.

8. The pharmaceutical agent according to claim 6 wherein each oxindole alkaloid is in the hydrochloride form and present as an aqueous solution having a concentration of between $10^{-3}\%$ and $10^{-6}\%$.

9. The pharmaceutical agent according to claim 6 wherein at least one oxindole alkaloid is selected from the group consisting of:

allo-isopteropodine, isomer A having the formula

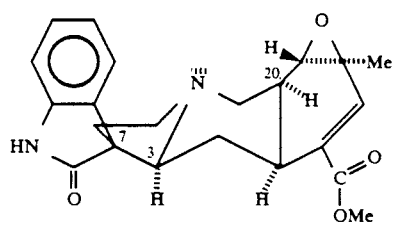

and allo-pteropodine, isomer B having the formula

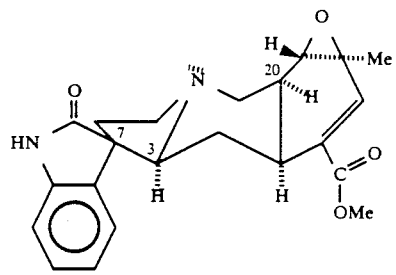

10. The pharmaceutical agent according to claim 6 wherein said alkaloid-catechine complex is produced from a ratio of ten parts by volume of aqueous catechine extract to one part by volume of aqueous oxindole alkaloid solution.

11. A method for preparing a plant extract for stimulating the immunological system, said plant extract containing an oxindole alkaloid being selected from the group consisting of isopteropodine and pteropodine, said method comprising:

providing root parts from Uncaria tomentosa (WILLD.) DC. of the order of Gentianales having a yellow-brown or dark red fresh bast, drying then pulverizing said root parts, moistening the dried, pulverized root parts with a solution of NH$_3$, redrying said moistened root parts, macerating said re-dried root parts to form a mixture, concentrating and extracting said mixture to make an aqueous phase, mixing said aqueous phase with solid Na$_2$CO$_3$ forming an alkalized aqueous phase, and extracting said alkalized aqueous phase to produce the plant extract.

12. A method for preparing the plant extract according to claim 11 wherein the drying step is carried out at a temperature slightly below the carbonizing temperature of the plant root.

13. A method for preparing the plant extract according to claim 11 wherein the concentration of the NH₃ solution in the moistening step in 10%.

14. A method for preparing the plant extract according to claim 11 wherein the re-dried root parts are macerated with ethyl acetate.

15. A method for preparing the plant extract according to claim 11 wherein the mixture in the concentrating and extracting step is subjected to 2% $H_2SO_4$.

16. A method for preparing the plant extract according to claim 11 wherein the aqueous solution in the concentrating and extracting step shows no positive Valser reaction.

17. A method for preparing the plant extract according to claim 11 wherein the mixing step is continued until the aqueous phase has an alkaline reaction at pH 8-9.

18. A method for preparing the plant extract according to claim 11 wherein the alkalized aqueous phase is repeatedly extracted with ethyl acetate.

19. A method for preparing the plant extract according to claim 11 wherein the plant extract produced is a raw alkaloid mixture.

20. A method for preparing the plant extract according to claim 11 wherein the dried, pulverized root parts are alkalized with 10% NH₃ making an eluant of a ratio of 1:10 which is extracted for two days at room temperature, filtered then concentrated to dryness before the moistening step.

21. A method for preparing the plant extract according to claim 11 wherein the oxindole alkaloid is an isomer of the allo-series.

22. A method for preparing the plant extract according to claim 1 wherein the oxindole alkaloid is selected from the group consisting of:
allo-isopteropodine, isomer A having the formula

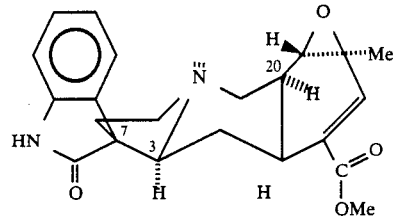

and allo-pteropodine, isomer B having the formula

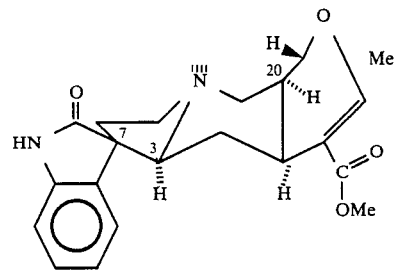

23. A method of preparing a plant extract according to claim 1 wherein said plant extract is dissolved in ether and HCl-gas to form an HCl precipitate from which the ether is separated and the HCl precipitate is washed again with anhydrous ether and then dried over phosphorpentoxide in a vacuum desiccator to form a water-soluble hydrochloride form of the plant extract.

24. A method of preparing a plant extract according to claim 11 wherein said plant extract is mixed one part by volume with ten parts aqueous catechine, stirred 24 hours at room temperature and freeze-dried to form an alkaloid-catechine complex of the plant extract.

* * * * *